(12) United States Patent
Powers et al.

(10) Patent No.: US 7,211,377 B1
(45) Date of Patent: *May 1, 2007

(54) METHOD FOR DETECTING THE PRESENCE OF DORMANT CRYPTOBIOTIC MICROORGANISMS

(75) Inventors: Linda S. Powers, Logan, UT (US); Christopher R. Lloyd, Logan, UT (US)

(73) Assignee: Microbiosystems, Limited Partnership, Cheyenne, WY (US)

( * ) Notice: Subject to any disclaimer, the term of this patent is extended or adjusted under 35 U.S.C. 154(b) by 294 days.

This patent is subject to a terminal disclaimer.

(21) Appl. No.: 10/817,649

(22) Filed: Apr. 2, 2004

Related U.S. Application Data

(63) Continuation-in-part of application No. 10/054,419, filed on Jan. 22, 2002, now Pat. No. 6,750,006.

(51) Int. Cl.
*C12Q 1/00* (2006.01)
*C12P 35/06* (2006.01)

(52) U.S. Cl. .............................. 435/4; 435/49

(58) Field of Classification Search ...................... None
See application file for complete search history.

(56) References Cited

U.S. PATENT DOCUMENTS

| | | | |
|---|---|---|---|
| 3,850,525 A | 11/1974 | Kaye | |
| 4,745,285 A | 5/1988 | Recktenwald et al. | |
| 4,900,934 A | 2/1990 | Peeters et al. | |
| 5,208,651 A | 5/1993 | Buican | |
| 5,294,799 A | 3/1994 | Aslund et al. | |
| 5,418,371 A | 5/1995 | Aslund et al. | |
| 5,424,959 A | 6/1995 | Reyes et al. | |
| 5,474,910 A | 12/1995 | Alfano | |
| 5,491,343 A | 2/1996 | Brooker | |
| 5,701,012 A | 12/1997 | Ho | |
| 5,760,406 A | 6/1998 | Powers | |
| 5,866,430 A | 2/1999 | Grow | |
| 5,968,766 A | 10/1999 | Powers | |
| 6,124,597 A | 9/2000 | Shehada et al. | |
| 6,139,800 A | 10/2000 | Chandler | |
| 6,750,006 B2 * | 6/2004 | Powers et al. ................. | 435/4 |

OTHER PUBLICATIONS

Alimova et al., "Native fluorescence and excitation spectroscopic changes in *Bacillus subtilis* and *Staphylcoccus aureu* bactera subjected to conditions of starvation", Applied Optics 42 (19): 4080-4087 (2003).*

Smith et al., "Detection of *Bacillus* endospores using total luminescence spectroscopy", Spectrochimica Acta Part A 60 : 2517-2521 (2004).*

* cited by examiner

*Primary Examiner*—Sandra E. Saucier
(74) *Attorney, Agent, or Firm*—Jones, Waldo, Holbrook & McDonough; K. S. Cornaby

(57) ABSTRACT

Method for the detection of dormant cryptobiotic microbes by detection of electromagnetic radiation emitted from intrinsic alkali earth metal pyridine dicarboxylic acid salts in the 710 nm to 860 nm region when excited with electromagnetic energy in the 610 nm to 680 nm region. Utilizing the novel lower energy emission of intrinsic calcium dipicolinic acid salts makes it possible to quickly detect bacterial spores, fungal spores and oocysts without the need for any added reagents, sample processing, or contact with the sample.

3 Claims, 5 Drawing Sheets

A  B

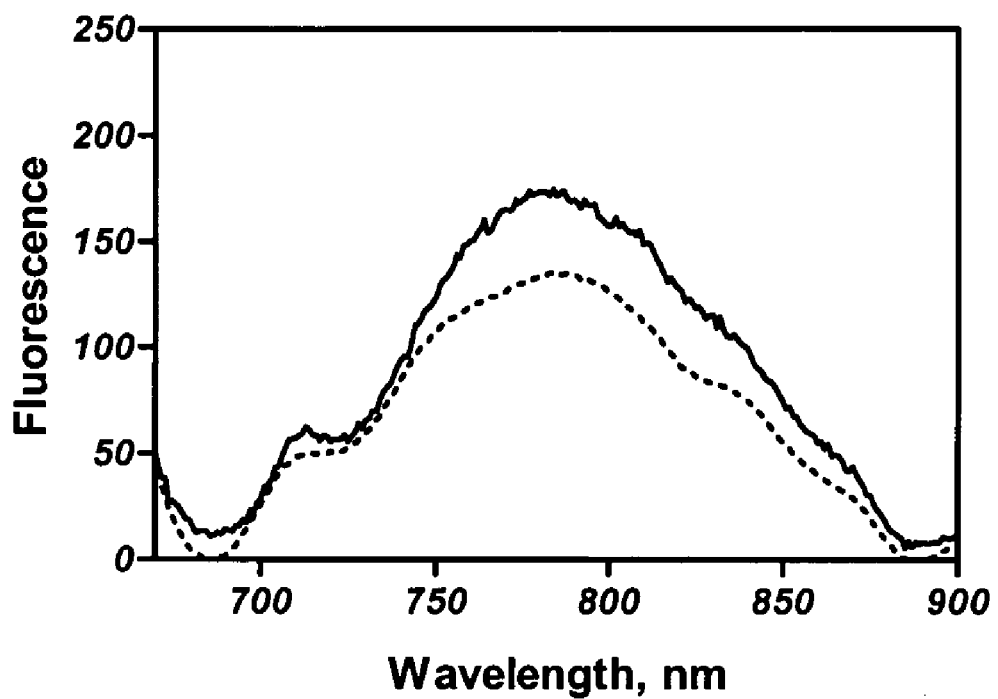

METHOD FOR DETECTING THE PRESENCE OF DORMANT CRYPTOBIOTIC MICROORGANISMS

CROSS-REFERENCE TO RELATED APPLICATIONS

This application is a continuation in part of U.S. patent application Ser. No. 10/054,419, now U.S. Pat. No. 6,750,006, filed Jan. 22, 2002, the entire contents of which are incorporated herein by reference.

FIELD OF THE INVENTION

This invention relates to a method and apparatus for sensing the presence of spores on surfaces, in air and in liquids.

BACKGROUND OF THE INVENTION

Determining the presence of bacterial endospores by detecting the presence of pyridine-2,6-dicarboxylic acid (dipicolinic acid) has been used by those skilled in the art for some time. This compound comprises a significant portion of viable spores, and is otherwise rare in nature (R. Lundin and L. Sacks, "High-resolution solid-state $^{13}C$ nuclear magnetic resonance of bacterial spores: Identification of the alpha-carbon signal of dipicolinic acid," Appl. Environ. Microbiol., vol. 54, no. 4, pp. 923–928, 1988). Various analytical methods are used to detect dipicolinic acid to indicate the presence of spores, including derivative spectroscopy (A. Warth, "Determination of dipicolinic acid in bacterial spores by derivative spectroscopy," Anal. Biochem., vol. 130, no. 2, pp. 502–505, 1983); intrinsic fluorescence (A. Alimova, A. Katz, H. E. Savage, M. Shah, G. Minko, D. V. Will, R. B. Rosen, S. A. McCormick and R. R. Alfano, "Native fluorescence and excitation spectroscopic changes in Bacillus subtilis and Staphylococcus aureus bacteria subjected to conditions of starvation," Appl. Opt., vol. 42, no. 19, pp. 4080–4087, 2003); luminescence following the addition of lanthanide salts (D. L. Rosen, C. Sharpless and L. B. McGown, "Bacterial spore detection and determination by use of terbium dipicolinate photoluminescence," Anal. Chem., vol 69, pp. 1082–1085, 1997); mass spectrometry (M. B. Beverly, K. J. Voorhees and T. L. Hadfield, "Direct mass spectrometric analysis of Bacillus spores," Rapid Commun. Mass Spectrom., vol. 13, no. 23, pp. 2320–2326, 1999); Fourier-transform infrared spectroscopy (H. Y. Cheung, J. Cui and S. Sun, "Real-time monitoring of Bacillus subtilis endospore components by attenuated total reflection Fourier-transform infrared spectroscopy during germination," Microbiology, vol. 145, pp. 1043–1048, 1999); Raman spectroscopy (U.S. Pat. No. 6,040,191 and H. Shibata, S. Yamashita, M. Ohe and I. Tani, "Laser Raman spectroscopy of lyophilized bacterial spores," Microbiol. Immunol., vol. 30, no. 4, pp. 307–313, 1986); and plasma chromatography coupled to gas chromatography (U.S. Pat. No. 6,672,133 B1).

Detection of endospores through the presence of calcium dipicolinate has been utilized in U.S. patents through detection of either the calcium and/or the dipicolinic acid. U.S. Pat. No. 6,498,041 B1 describes capture of spores based upon a molecular recognition of spore coat components followed by detection of $Ca^{2+}$ by way of addition of fluorescent calcium-binding dyes excited by light in the visible spectrum. U.S. Pat. No. 6,599,715 and U.S. patent application Ser. No. 10/355,462 teaches detection of dipicolinic acid by way of luminescence from terbium dipicolinate when excited with ultraviolet light.

Furthermore, the presence of dipicolinic acid (or other pyridine dicarboxylic acid analogs with closely related chemical structures) has been reported for other cryptobiotic microorganisms. (Cryptobiotic describes microbes capable of achieving a dormant state). Specifically, dipicolinic acid has been utilized to detect Clostridium spores, (M. W. Tabor, J. MacGee and J. W. Holland, "Rapid determination of dipicolinic acid in the spores of Clostridium species by gas-liquid chromatography," Appl. Environ. Microbiol., vol. 31, no. 1, pp. 25–28, 1976); Sporosarcina spores (C. A. Loshon and P. Setlow, "Levels of small molecules in dormant spores of Sporosarcina species and comparison with levels in spores of Bacillus and Clostridium species," Can. J. Microbiol., vol. 39, no. 2, pp. 259–262, 1993); Sarcina spores (R. S. Thompson and E. R. Leadbetter, "On the isolation of dipicolinic acid from endospores of Sarcina ureae," Arch. Mikrobiol., vol. 45, pp. 27–32, 1963); and Metabacterium spores (S. Stunkel, J. Alves and I. Kunstyr, "Characterization of two 'Metabacterium' sp. from the gut of rodents. Heteroxenic cultivation and proof of dipicolinic acid in 'M. polyspora,'" Folia Microbiol. (Praha), vol. 38, no. 3, pp. 171–175, 1993). Pyridine dicarboxylic acid compounds are found in these and other cryptobiotic (spore-forming) microorganisms.

U.S. patent application Ser. No. 10/054,419, filed Jan. 22, 2002, and incorporated herein by reference, discloses a method and apparatus for the detection of microbes on non-living surfaces and samples in which samples are exposed to electromagnetic radiation of numerous specific energies capable of exciting fluorescence from various metabolites, cofactors and cellular and spore components. Thus, the microbial cells and spores to be sampled (and more specifically the excited metabolites, cofactors and other cellular, viral and/or spore components) contained therein emit fluorescence that can be measured. The collected fluorescence signals (associated with the signals emitted from the cellular/viral/spore components) are analyzed with a method capable of (1) removing any background and/or reflected and scattered excitation signal, and (2) comparing the relative fluorescent signals of metabolites, cofactors and spore components to known physiological ranges. Specifically, U.S. patent application Ser. No. 10/054, 419 teaches the detection of spores by excitation of calcium dipicolinic acid with ultraviolet electromagnetic radiation (light) in the 270 nm–290 nm and 310 nm–330 nm ranges (singly or concurrently), with detection of fluorescence energies in the 460 nm–480 nm and 400 nm–430 nm regions, respectively. The aforementioned application also teaches the detection of spores by excitation with electromagnetic radiation (light) in the 610 nm–670 nm range with detection of light energies in the 730 nm–800 nm region. This novel emission was observed in emission spectra from aqueous bacterial spore samples and in a non-viable Bacillus thuringiensis cell sample as illustrated in FIG. 3F of the aforementioned application. Utilizing these novel lower energy excitation and emission ranges for the detection of spores is beneficial as (1) there is little interference and/or overlap from other microbial fluorophores, (2) background interference from biologically-derived organic surfaces is greatly reduced, and (3) greater excitation penetration depth into the sample can be expected. This current specification demonstrates that the beneficial lower energy excitation and emission signals arise from calcium dipicolinate and teaches the benefits of using these excitation sources for the detection of spores.

As is known to those skilled in the art, fluorescence is a form of luminescence. [Fluorescence and phosphorescence are defined as types of photoluminescence spectrometry (J. D. Ingle, Jr. and S. R. Crouch, *Spectrochemical Analysis*, pp. 438, 1988, Prentice-Hall, Inc.).] The primary difference between fluorescence and phosphorescence is the emission lifetimes (I. Tinoco, Jr., K. Sauer and J. C. Wang, *Physical Chemistry: Principles and Applications in Biological Sciences*, pp. 577, 1995, Prentice-Hall). (Fluorescence refers to emission lifetimes that are in the microsecond and shorter range; phosphorescence refers to emission lifetimes are typically in the millisecond or longer range.) Thus, without data of emission lifetimes, phosphorescence and fluorescence are experimentally indistinguishable using traditional emission spectroscopy. In this case, the 'apparent fluorescence' from the intrinsic chromophores (chemical components that absorb excitation energies and emit radiation of lower energy) may arise from either phosphorescence or fluorescence. Detection of apparent fluorescence from intrinsic microbial components confers the ability to detect dormant cryptobiotic microbes (1) without making physical contact with the sample, (2) very rapidly, and (3) without the use of any added reagents.

As can be readily appreciated, it would be very useful to be able to determine the presence of dormant (cyrptobiotic and/or spore-forming) microorganisms in hospitals, food preparation areas, water supplies, buildings and on the battlefield as these microbes require the greatest effort to eradicate. This method and apparatus, as an object of the invention, should be operated inexpensively and rapidly in, for example, food production facilities.

SUMMARY OF THE INVENTION

The present invention provides a method to detect cryptobiotic microorganisms by means of detecting emissions in the near-infrared arising from excitation of intrinsic components with light in the red region of the visible spectrum. The concepts of the present invention reside in a method and apparatus for the detection of cryptobiotic (dormant, spore-forming) microbes in which samples are exposed to electromagnetic radiation in the 610 nm–680 nm region and detected from emissions in the 730 nm–860 nm region. The spores to be sampled (more specifically the calcium dipicolinate contained therein) emit electromagnetic energy that can be measured. The collected emission signal emitted from the calcium pyridine dicarboxylic acid salts) is analyzed with a method capable of removing any background, reflected excitation energies and/or scattered light. Thus, the method and apparatus of the present invention provides an inexpensive and rapid way in which to scan samples to detect and quantitate the presence of microbial contamination without contact with the sample. Being able to evaluate microbial contamination in a sample without contact reduces the risk of introducing contamination.

It is an object of the invention to provide a method and apparatus for use in the detection of cryptobiotic microbial contamination on foods in which emission signals arising from calcium pyridine dicarboxylic acid compounds are detected in the 730 nm–860 nm region when excited by electromagnetic radiation in the 610 nm–680 nm region, allowing dormant microbial contamination on foods to be determined quantitatively without contact with said food.

It is another object of the invention to provide a method and apparatus that can be used in the detection of cryptobiotic microbial contamination on non-living surfaces, in liquids and air. As a specific object of the invention, the method and apparatus can be used to find cryptobiotic microbes and microbial contamination inexpensively and rapidly in, for example, health-care facilities, research laboratories, water treatment and testing stations, buildings and on the battlefield.

It is yet another object of the invention to provide a method and apparatus for use in the detection of microbial contamination on non-living surfaces and in liquid and air samples in which the emission of calcium pyridine dicarboxylate compounds are excited by electromagnetic radiation in the 610 nm–680 nm region and detected in the 730 nm–860 nm region, allowing microbial contamination in samples to be determined without contact with said sample.

In accordance with this form of the invention, it is frequently desirable to utilize light source(s) emitting electromagnetic radiation around 630 nm. In accordance with the present form of the invention, the light emitted by the light source is specific to or filtered to pass therethrough electromagnetic radiation of energies specific to excite calcium dipicolinate.

In accordance with another embodiment of the invention, it is possible, and sometimes desirable, to direct electromagnetic radiation around 580 nm at the sample. The 580 nm light excites flavins and heme compounds in microbes, some of whose emission is self-absorbed by the sample sequentially exciting calcium dipicolinate with emission in the 610 nm–680 nm range. The apparent fluorescent emissions of the sample are collected and analyzed as described previously.

In accordance with another embodiment of the invention, it is possible, and sometimes desirable, to direct electromagnetic radiation of energies capable of exciting calcium dipicolinate and also energies that do not interact with the spores. Thus, in accordance with this embodiment of the invention, the resulting fluorescent signal emanating from the sample (both from the microbial components and those simply reflected and/or scattered from the sample) can be measured and the presence of microbes determined by comparing the ratios of the emitted signals from the microbes compared to those reflected/scattered from the sample.

In accordance with the practice of the invention, a sensor is used to detect not only the emission generated by the intrinsic chromophores but also to detect the background, reflected and/or scattered electromagnetic radiation. This serves to normalize the signal and compensate for variations in the signal that might otherwise be caused by the use of varying distances between the detector and the sample being scanned and variations between different samples or surfaces.

It has also been found that by rapidly changing the electromagnetic radiation directed to the sample at frequencies different than 60 Hertz, the effects of ambient light (and particularly fluorescent light) can be substantially minimized. The modulation of the excitation energy also permits the sensor to be moved to direct the electromagnetic radiation to various parts of a sample without substantially affecting the accuracy of the measurement of the microbial content.

The microbial detection method and apparatus described herein is able to determine the presence and physiological status of cryptobiotic microorganisms while at the same time requiring no reagents, no contact with the sample, is inexpensive to perform and delivers 'real-time' results. These, and other objects, features and advantages of the present invention will become apparent upon review of the following detailed descriptions of the disclosed embodiments and the appended claims.

BRIEF DESCRIPTION OF THE DRAWINGS

FIG. 9 shows the emission spectra (630 nm excitation) of bacterial (—) and yeast (-----) spore solutions.

DETAILED DESCRIPTION OF THE INVENTION

Figure 1:
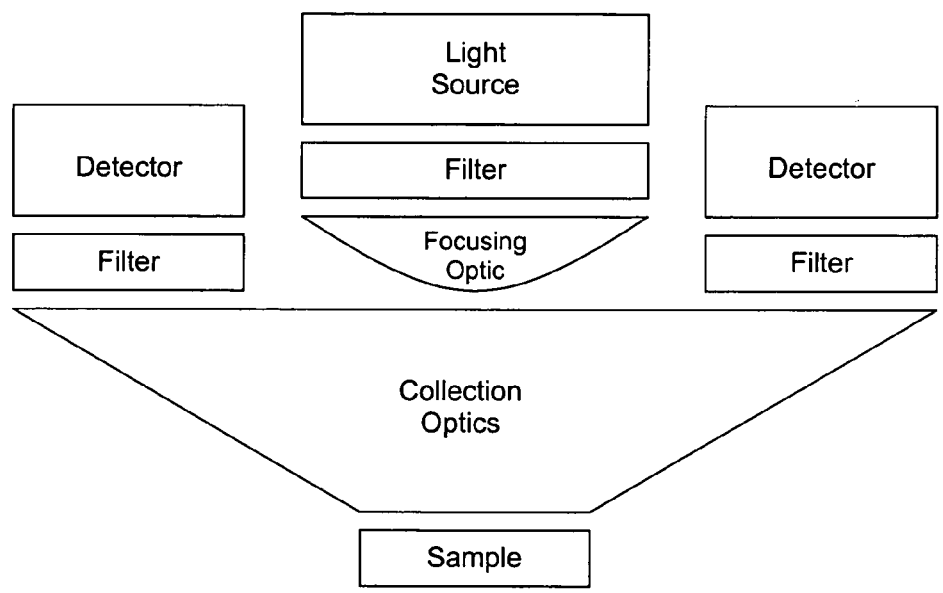
FIG. 1 is a block diagram of an instrument that can be used to practice the most basic features of the invention.
Figure 2:
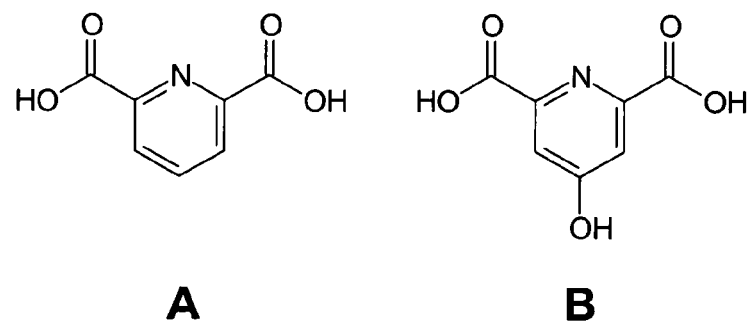
FIG. 2 shows the chemical structures of dipicolinic acid (pyridine-2,6-dicarboxylic acid, A) and chelidamic acid (4-hydroxypyridine-2,6-dicarboxylic acid, B).
Figure 3:
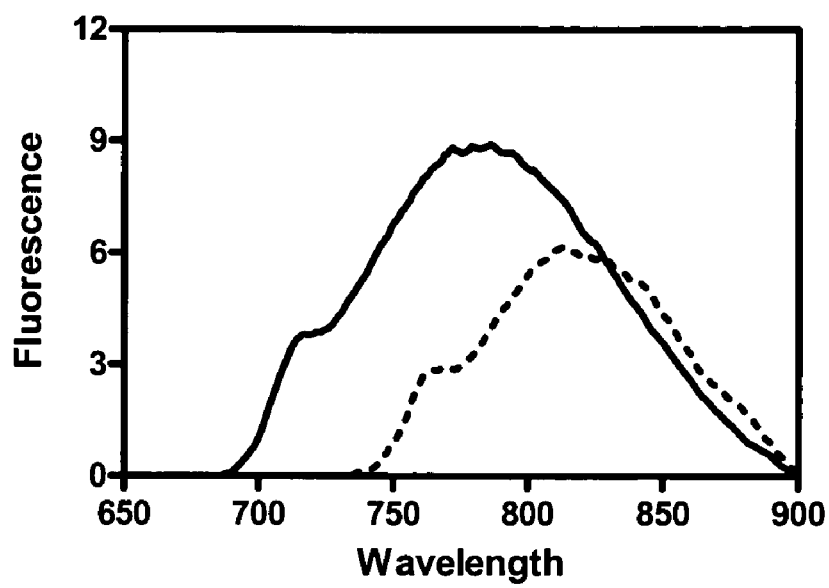
FIG. 3 shows the emission spectra of 20 mM solutions of calcium dipicolinate (—) when excited at 630 nm and calcium chelidamate (-----) when excited at 670 nm.

The basic elements for the apparatus that can be used to carry out one embodiment of the method described by this invention are shown as a block diagram in FIG. 1. The apparatus consists of a light source, excitation filters, focusing optics, collection optics, emission filters and detectors. Electromagnetic radiation is directed from the light source towards the sample, passing through the excitation filters and focusing optics if necessary, to excite the intrinsic chromophores in the sample. The scattered and reflected excitation radiation, along with the emitted radiation, are collected with the collection optics and directed towards the detectors. Emission filters ensure that only the energies of interest are measured.

Figure 4:
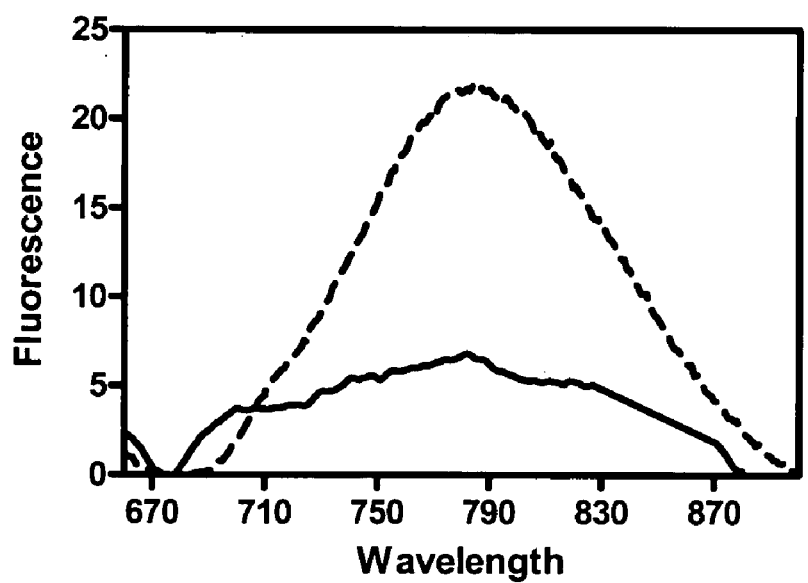
FIG. 4 shows the emission spectra of solid and a solution of calcium dipicolinate when excited with radiation of 630 nm. The solid line shows the emission spectra of the solid salt and the dashed line shows the emission spectra of the saturated solution.
Figure 5:
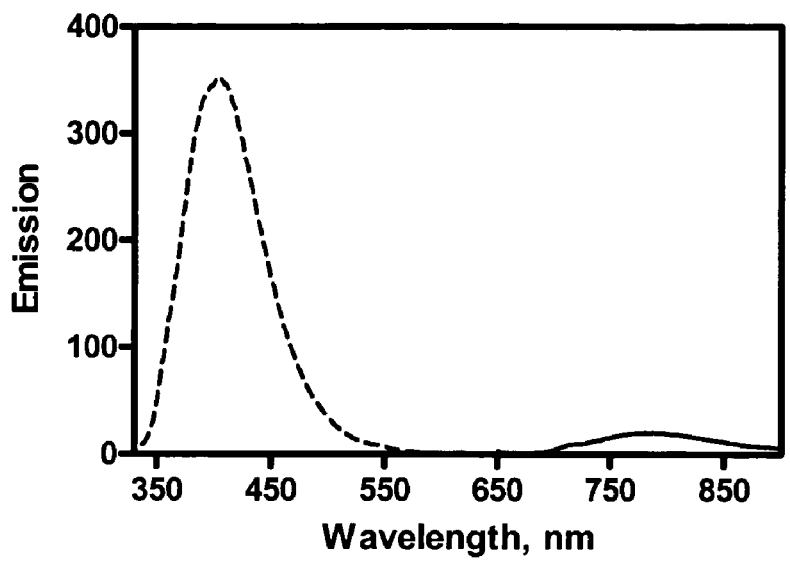
FIG. 5 shows the emission spectra of aqueous calcium dipicolinate when excited at 315 nm (—) and 630 nm (—).

Various embodiments of the invention, including different configurations and utilizing diverse components, are possible. The fundamental components for this microbial detection method permit: (1) the excitation of calcium pyridine dicarboxylate salts in the 610 nm to 680 nm region, (2) collection and detection of emitted electromagnetic radiation in the 710 nm to 860 nm region, background (ambient) light, reflected excitation light and scattered light energies, and (3) analysis of the detected signals with a method that is able to correct for background interferences. The configuration and components employed in any apparatus using this method should be matched with the application requirements and expected interferences.

It is possible, and sometimes desirable, to utilize a light source that provides a broad band illumination. The kind of light source employed is influenced by its ability to produce electromagnetic radiation of the wavelength required to excite the intrinsic microbial components of interest. Additionally, it is sometimes desirable to use a pulsed light source allowing measurement of the environmental background during the off cycle. The light sources that can be used include lamps with various bulbs (e.g., mercury, tungsten, deuterium, xenon), light emitting diodes (LEDs), and diode lasers specific for the required excitation energies. The kind of light source used depends upon the intensity of excitation radiation needed and detection limit required.

The excitation and emission filters used in the various embodiments of the invention include interference filters, impregnated glass, series of cutoff filters, gelatin filters, monochrometers, gratings, rugate filters and the like. The light cutoff characteristics of the emission filters used depend on how much of the scattered and reflected excitation radiation signal can be tolerated by the analysis method or what detection limit is required. If light sources having only the energies of interest are employed, the excitation filters may not be necessary; if the light source is collimated (such as a laser) then the focusing optic may not be required. (The purpose of the focusing optic is to direct the excitation radiation to the sampling area or volume.) It is important to note that with multi-photon excitation it is possible to use light sources with energies less than the excitation energies of the chromophores of interest.

The purpose of the collection optics is to deliver the light emitted from the excited microbial chromophores and that scattered and reflected from the sample to the detectors. If interference filters are utilized to discriminate these emission energies, then the collected light needs to be collimated for these filters to work optimally. Fiber-optic cables can also be used to both deliver the excitation radiation to the sample and to collect the emitted radiation and direct it towards the detectors. It is possible, and sometimes desirable, to utilize polished metal reflective, sapphire, fused silica, quartz, $MgF_2$, and/or $CaF_2$ optical components as many optical components exhibit fluorescence in the ultraviolet and visible range.

The detectors are used to convert the emitted electromagnetic radiation into an electrical signal that can be measured. Numerous detectors, with different sensitivities, can be utilized in the embodiments of the invention: photomultiplier tubes (PMTs), avalanche photodiodes (APDs), pin diodes, CCDs, and the like. The detector chosen would depend upon the energy of the radiation to be detected, the strength of the emission signal, and the required detection limit of the apparatus. The collected emission energies, having been converted to amplified electrical signals, are analyzed with a method capable of removing any background emission, reflected excitation light and/or scattered excitation signal contributions.

FIG. 2 shows the chemical structures of dipicolinic acid (pyridine-2,6-dicarboxylic acid) and chelidamic acid (4-hydroxypyridine-2,6-dicarboxylic acid). FIG. 3 shows the emission spectra of calcium dipicolinate (excited at 630 nm) and calcium chelidamate (excited at 670 nm). Emission of energy in the 710 nm to 860 nm region when excited with electromagnetic energy in the 610–680 nm region is a property of alkali earth metal pyridine dicarboxylic acid salts, demonstrating the utility of this emission from calcium dipicolinate (or other intrinsic pyridine dicarboxylic acid analogs with closely related chemical structures resulting from either alternate biosynthetic pathways or subsequent innate reactions of dipicolinate) for the detection of dormant cryptobiotic microorganisms.

FIG. 4 shows the emission spectra a solid sample and a saturated solution of calcium dipicolinate when excited with radiation of 630 nm. The solid line shows the emission spectra of the solid salt and the dashed line shows the emission spectra of the saturated solution. The spectra of both solid and aqueous calcium dipicolinate show emission at around 780 nm, though the spectrum of the solid sample is depressed relative to the solution. (The emission of the solid calcium dipicolinate spectrum may be quenched due to concentration.) FIG. 5 shows the emission spectra of aqueous calcium dipicolinate when excited at 315 nm (----) and 630 nm (—), illustrating the relative signal strength of the novel, low-energy emission signal relative to the known calcium dipicolinate fluorescence emission (R. Nudelman, N. Feay, M. Hirsch, S. Efrima and B. Bronk, "Fluorescence of Dipicolinic Acid as a Possible Component of the Observed UV Emission Spectra of Bacterial Spores" SPIE vol. 3533, pp. 190–195, 1998).

Figure 6:
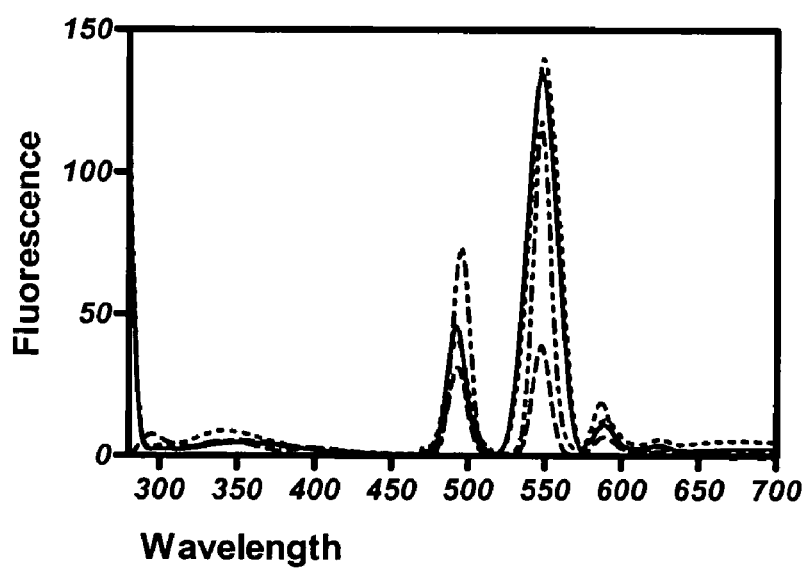
FIG. 6 shows the emission spectra (270 nm excitation) of a pure calcium dipicolinic acid solution (—), the aqueous calcium dipicolinate extract from *Bacillus thuringiensis* spores (—), the aqueous calcium dipicolinate extract from *Saccharomyces cerevisiae* spores (-----), and the aqueous calcium dipicolinate extract from *Cryptosporidium parvum* oocysts (-••-••-) to which $Tb^{3+}$ had been added.
Figure 7:
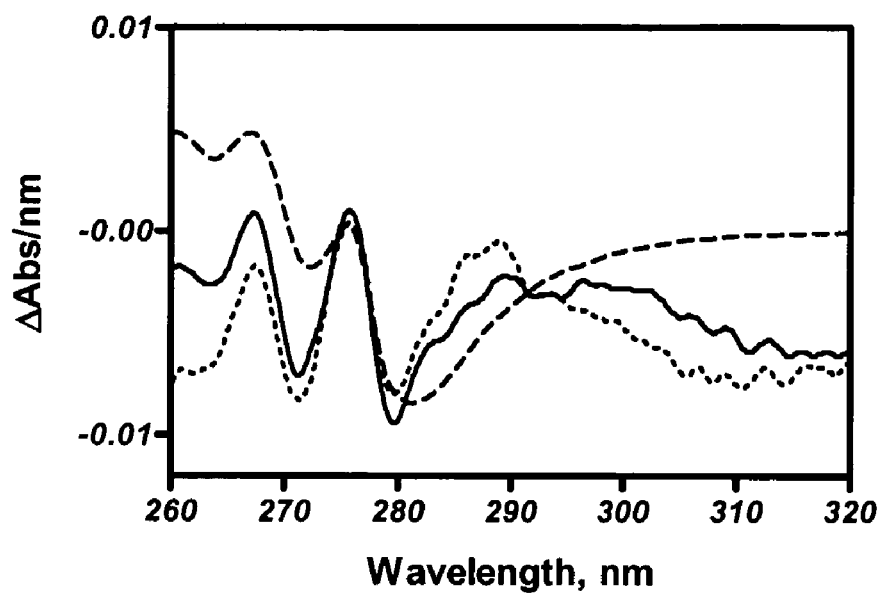
FIG. 7 shows the derivative optical density spectra of a pure calcium dipicolinic acid solution (—), the aqueous calcium dipicolinate extract from *Bacillus thuringiensis* spores (—), and the aqueous calcium dipicolinate extract from *Saccharomyces cerevisiae* spores (-----).
Figure 8:
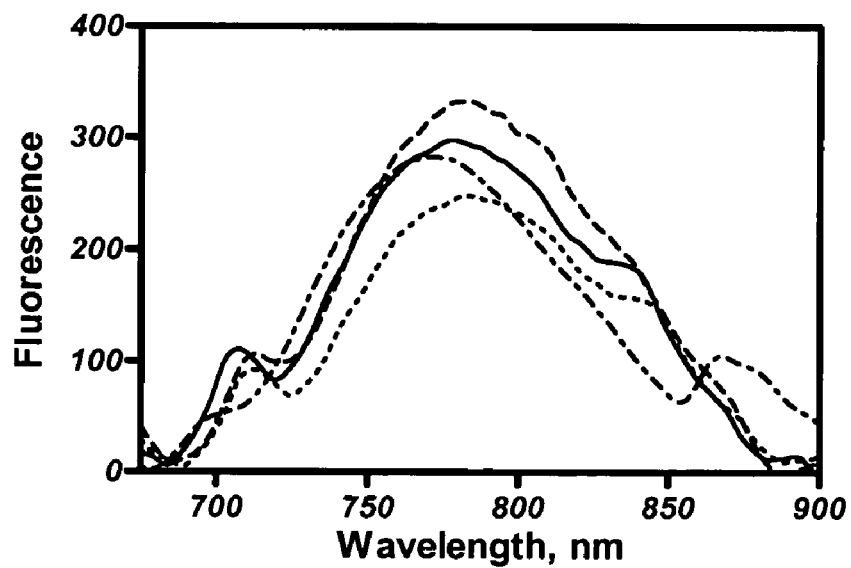
FIG. 8 shows the emission spectra (630 nm excitation) of bacterial spore solutions of *Bacillus anthracis* (—), *Bacillus megaterium* (-----), *Bacillus subtilis* (-----) and *Bacillus thuringiensis* (-••-••-).

FIG. 6 shows the emission spectra (270 nm excitation) of a pure calcium dipicolinic acid solution (----), the aqueous extract from *Bacillus thuringiensis* spores (—), the aqueous extract from *Saccharomyces cerevisiae* spores (----), and the aqueous extract from *Cryptosporidium parvum* oocysts to which $Tb^{3+}$ had been added (according to the method described in *Anal. Chem.*, vol 69, pp. 1082–1085, 1997). FIG. 7 shows the derivative optical density spectra of a pure calcium dipicolinic acid solution (----); this figure also shows the aqueous extracts from *Bacillus thuringiensis* spores (—), and *Saccharomyces cerevisiae* spores (----) to which $Ca^{2+}$ had been added (according to the method described in *Anal. Biochem.*, vol. 130, no. 2, pp. 502–505, 1983). These figures clearly show the presence of periodic table Group II (alkali earth metals, including $Mg^{2+}$, $Ca^{2+}$, and the like) pyridine dicarboxylic acid compounds in a variety of dormant cryptobiotic microorganisms: yeast spores, bacterial spores and paramecium oocysts. FIG. 8 shows the emission spectra (630 nm excitation) of bacterial spore solutions of *Bacillus anthracis, Bacillus megaterium, Bacillus subtilis* and *Bacillus thuringiensis*. The presence of the calcium dipicolinic acid emission between 710 nm and 860 nm shows the ubiquitous presence of calcium dipicolinate in a number of bacterial spores. FIG. 9 shows the emission spectra (630 nm excitation) of bacterial (*Bacillus* spp.) and yeast (*Saccharomyces* spp.) spore solutions, illustrating the utility of using the 710 nm–860 nm emission for detection of fungal as well as bacterial spores.

Utilizing the novel lower energy emission of intrinsic alkali earth metal pyridine dicarboxylic acid salts makes it possible to quickly detect dormant cryptobiotic microbes without the need for any added reagents, sample processing, or contact with the sample. The embodiments of the present invention described above are intended to be merely exemplary, with other configurations, variations and modifications utilizing the aforementioned basic ideas available to those skilled in the art without departing from the spirit of the invention. The scope of this method to detect dormant cryptobiotic microbes includes utilization of the emission of light from intrinsic alkali earth metal pyridine dicarboxylic acid salts in the 710 nm to 860 nm region when excited with electromagnetic energy in the 610 nm to 680 nm region. An important embodiment includes excitation of this intrinsic chromophore with subsequent analysis of the detected emission with methods that concurrently account for background signals, scattered excitation signal and reflected excitation signal. All variations, modifications and configurations are intended to be within the scope of the present invention as defined in the appended claims.

What is claimed is:

1. A method for the detection of dormant cryptobiotic microbes comprising:
   a. exciting the intrinsic dormant cryptobiotic microbial chromaphore with a specific range of electromagnetic radiation wavelength between 610 nm and 680 nm; whereby said microbes containing intrinsic chromophores are excited to emit electromagnetic radiation;
   b. detecting the emitted electromagnetic radiation signals from the excited microbial chromophores in the 710 nm to 860 nm range; and
   c. removing the background, reflected excitation and/or scattered electromagnetic radiation signals from the emission signal by analysis, in order to detect the presence of dormant cryptobiotic microbes.

2. A method as set forth in claim 1, wherein said microbe chromophores are selected from the group consisting of alkali earth metal-pyridine dicarboxylic acid salts.

3. The method of claim 1 wherein the dormant cryptobiotic microbes to be detected include bacterial endospores, fungal spores, and protozoa oocysts.

* * * * *